(12) United States Patent
Jae et al.

(10) Patent No.: US 10,335,778 B2
(45) Date of Patent: Jul. 2, 2019

(54) CATALYST FOR PRODUCING GAMMA-VALEROLACTONE, METHOD FOR PREPARING THE SAME AND METHOD FOR MANUFACTURING GAMMA-VALEROLACTONE USING THE SAME

(71) Applicant: KOREA INSTITUTE OF SCIENCE AND TECHNOLOGY, Seoul (KR)

(72) Inventors: Jungho Jae, Seoul (KR); Haryo Pandu Winoto, Seoul (KR); Jeong-Myeong Ha, Seoul (KR); Hyun Joo Lee, Seoul (KR); Dong Jin Suh, Seoul (KR); Byoung Sung Ahn, Seoul (KR)

(73) Assignee: KOREA INSTITUTE OF SCIENCE AND TECHNOLOGY, Seonbuk-Gu, Seoul (KR)

( * ) Notice: Subject to any disclaimer, the term of this patent is extended or adjusted under 35 U.S.C. 154(b) by 0 days.

(21) Appl. No.: 16/043,161

(22) Filed: Jul. 24, 2018

(65) Prior Publication Data

US 2019/0134616 A1    May 9, 2019

(30) Foreign Application Priority Data

Nov. 6, 2017  (KR) .................. 10-2017-0146735

(51) Int. Cl.
| | | |
|---|---|---|
| *B01J 29/70* | (2006.01) | |
| *B01J 27/19* | (2006.01) | |
| *B01J 37/02* | (2006.01) | |
| *C07D 307/33* | (2006.01) | |
| *B01J 21/06* | (2006.01) | |

(52) U.S. Cl.
CPC ........... *B01J 29/7007* (2013.01); *B01J 21/06* (2013.01); *B01J 27/19* (2013.01); *B01J 37/0201* (2013.01); *C07D 307/33* (2013.01); *B01J 2229/18* (2013.01)

(58) Field of Classification Search
CPC .......................... B01J 29/7007; C07D 307/33
See application file for complete search history.

(56) References Cited

U.S. PATENT DOCUMENTS

| | | | |
|---|---|---|---|
| 8,399,688 | B2 | 3/2013 | Dumesic et al. |
| 9,199,955 | B2 | 12/2015 | Corma Canos et al. |
| 9,487,712 | B2 | 11/2016 | Shuai et al. |
| 2013/0204015 | A1 | 8/2013 | Jacquot et al. |

FOREIGN PATENT DOCUMENTS

| | | |
|---|---|---|
| CN | 103012334 A | 4/2013 |
| CN | 104557801 A | 4/2015 |
| WO | 2011124578 A1 | 10/2011 |

OTHER PUBLICATIONS

Shanhui Zhu et al., "Integrated Conversion of Hemicellulose and Furfural into y-Valerolactone over Au/ZrO2 Catalyst Combined with ZSM-5", ACS Catalysis, 2016, pp. 2035-2042, vol. 6.

Haryo Pandu Winoto et al., "Production of gamma-valerolactone from furfural by a single-step process using Sn—Al Beta zeolites: Optimizing the catalyst acid properties and process conditions," Journal of Industrial and Engineering Chemistry, 2016, pp. 62-71, vol. 40, Elsevier B.V.

Hu Li et al., "Efficient valorization of biomass to biofuels with bifunctional solid catalytic materials," Progress in Energy and Combustion Science, 2016, pp. 98-194, vol. 55, Elsevier Ltd.

Margarida M. Antunes et al., "One-pot conversion of furfural to useful bio-products in the presence of a Sn,Al-containing zeolite beta catalyst prepared via post-synthesis routes," Journal of Catalysis, 2015, pp. 522-537, vol. 329, Elsevier Inc.

*Primary Examiner* — Golam M Shameem
(74) *Attorney, Agent, or Firm* — Cantor Colburn LLP

(57) ABSTRACT

Disclosed are a heteropolyacid catalyst for producing gamma-valerolactone, which is supported on M-Beta zeolite (M=Sn, Ti, Zr or Hf), and a method for preparing the same and a method for manufacturing gamma-valerolactone using the catalyst. The catalyst has an effect of producing gamma-valerolactone from biomass-derived furfural at a high yield through a one-pot process.

17 Claims, 2 Drawing Sheets

CATALYST FOR PRODUCING GAMMA-VALEROLACTONE, METHOD FOR PREPARING THE SAME AND METHOD FOR MANUFACTURING GAMMA-VALEROLACTONE USING THE SAME

BACKGROUND OF THE INVENTION

Field of the Invention

The present specification discloses a heteropolyacid catalyst for producing gamma-valerolactone, which is supported on M-Beta zeolite (M=Sn, Ti, Zr or Hf), and a method for preparing the same and a method for manufacturing gamma-valerolactone using the catalyst.

[Explanation on Nationally Supported Research and Development]

This research has been carried out under the supervision of the Korea Institute of Science and Technology with the support of the Ministry of Science, ICT, and Future Planning (specialized organization for research management: National Research Council of Science and Technology, title of research project: Development of next generation fuel/material production technology by integrated utilization of woody biomass, project assignment number: CAP-11-4-KIST).

Also, this research has been carried out under the supervision of the University of seoul Industry-Academia Collaboration Foundation with the support of the Ministry of Trade, Industry and Energy (specialized organization for research management: Korea Institute of Energy Technology Evaluation and Planning, title of research project: Development of fuel production technology for power generation/transportation from thermochemistry-microorganism complex process of lignin by-product, project assignment number: 1415148326).

Description of the Related Art

Lignocellulose, such as wood and herbaceous materials, is constituted in the form of biopolymers of cellulose, hemicellulose, and lignin, and glucose and xylose can be separated therefrom through appropriate pretreatment and saccharification processes.

Glucose can be converted into a bioalcohol fuel or various chemical products through a biological process, but xylose, which is composed of five carbon atoms, is a saccharide that is hardly converted into a bioalcohol through a biological process and is a raw material that is not suitable for use in the bioalcohol production process. Hence, the economic efficiency of the bioalcohol production process can be increased when xylose can be converted into a useful fuel or chemical product by a chemical conversion method.

It is essential to convert xylose into a highly reactive intermediate platform compound at first in order to chemically convert xylose into a fuel. In particular, furfural which is obtained through the dehydration reaction of xylose has been intensively studied as a starting material for chemical conversion. For example, a chemical process has been reported in which furfural is converted into a high-carbon fuel precursor through an aldol condensation reaction with acetone and then converted into gasoline and diesel-grade hydrocarbon liquid fuel through a hydrodeoxygenation reaction (U.S. Pat. No. 9,487,712B2). In a similar concept, a chemical process has also been reported in which furfural is converted into 2-methylfuran through a hydrogenation reaction and then converted into a high-carbon fuel precursor through trimerization of 2-methylfuran (U.S. Pat. No.9,199,955B2).

Gamma-valerolactone is a biomass-derived compound that has been attracting much attention recently. It is a versatile platform compound that can be used as environmentally friendly solvent, fuel additive, high-carbon fuel precursor, biopolymer precursor, and the like and can be produced through a hydrogenation reaction of levulinic acid, a derivative of biomass hexose such as glucose by a dehydration reaction. However, biomass hexose can be easily converted into a bioalcohol and the like through a biological process, and it is thus required to develop a chemical process technique for producing gamma-valerolactone from xylose, an unused saccharide.

According to the prior art, it is possible to produce gamma-valerolactone from xylose-derived furfural, but there is a problem that the number of unit processes required increases and the cost of the processes increases since a multistep chemical reaction is required. For example, in order to produce gamma-valerolactone from furfural, three steps of chemical processes are required in total, which include 1) conversion of furfural into furfuryl alcohol through a hydrogenation reaction, 2) conversion of furfuryl alcohol into levulinic acid through a ring-opening reaction, and 3) conversion of levulinic acid into gamma-valerolactone through a hydrogenation reaction. The existing techniques are based on a multistep process in which these three steps of reactions are independently separated, and some techniques suggest a process in which the first and second reactions are combined. Hence, it is required to develop a catalyst capable of producing gamma-valerolactone at a high selectivity through a one-pot process and a process in order to lower the process cost and production cost of gamma-valerolactone derived from xylose.

SUMMARY OF THE INVENTION

In an aspect, the present specification is intended to provide a catalyst for producing gamma-valerolactone, which is capable of converting furfural derived from an unused saccharide into gamma-valerolactone through a one-pot process.

In another aspect, the present specification is intended to provide a method for preparing the catalyst for producing gamma-valerolactone.

In still another aspect, the present specification is intended to provide a method for manufacturing gamma-valerolactone using the catalyst.

In an aspect, the technique disclosed herein provides a catalyst for producing gamma-valerolactone, containing Beta zeolite substituted with a metal; and a heteropolyacid supported on the zeolite.

In an exemplary embodiment, the metal may be one or more selected from Group 4 consisting of titanium (Ti), zirconium (Zr), and hafnium (Hf).

In an exemplary embodiment, the metal may be tin (Sn).

In an exemplary embodiment, the zeolite substituted with a metal may be prepared by a method including removing aluminum from Al-Beta zeolite and mixing the dealuminated Si-Beta zeolite with a metal precursor and then performing a heat treatment to substitute the zeolite skeleton with a metal.

In an exemplary embodiment, the catalyst may be for producing gamma-valerolactone from furfural.

In an exemplary embodiment, a content of the metal may be 1 to 10 wt % based on a total weight of the catalyst.

In an exemplary embodiment, the heteropolyacid may have a formula $H_nXM_{12}O_{40}$ where X may be a center element of phosphorus (P), silicon (Si), germanium (Ge) or arsenic (As), M may be a coordinating element including tungsten (W) or molybdenum (Mo), and n may be an integer more than 0.

In an exemplary embodiment, the heteropolyacid may be one or more selected from the group consisting of 12-tungstophosphoric acid ($H_3PW_{12}O_{40}$), 12-tungstosilicic acid ($H_4SiW_{12}O_{40}$), 12-molybdophosphoric acid ($H_3PMo_{12}O_{40}$), and 12-molybdosilicic acid ($H_4SiMo_{12}O_{40}$).

In an exemplary embodiment, the heteropolyacid may be supported in an amount of 1 to 10 parts by weight based on 100 parts by weight of a total weight of zeolite.

In another aspect, the technique disclosed herein provides a method for preparing the catalyst for producing gamma-valerolactone described above, the method including: impregnating Beta zeolite substituted with a metal with a heteropolyacid solution; and calcining the impregnated catalyst.

In an exemplary embodiment, a solvent of the heteropolyacid solution may be an alcohol solvent having 1 to 6 carbon atoms.

In an exemplary embodiment, the impregnating method may be an incipient wetness impregnation in which a heteropolyacid solution in an amount corresponding to a pore volume of zeolite is gradually added to and supported on the zeolite.

In an exemplary embodiment, a calcination temperature may be 100° C. to 400° C.

In still another aspect, the technique disclosed herein provides a method for manufacturing gamma-valerolactone, the method including: conducting a reaction for producing gamma-valerolactone using the catalyst for producing gamma-valerolactone described above.

In an exemplary embodiment, the reaction for producing gamma-valerolactone may be conducted by mixing furfural and an alcohol solvent with the catalyst.

In an exemplary embodiment, the reaction for producing gamma-valerolactone may be conducted at 120° C. to 180° C.

In an exemplary embodiment, the reaction for producing gamma-valerolactone may be conducted for 6 to 48 hours.

In an aspect, the technique disclosed herein has an effect of providing a heteropolyacid catalyst for producing gamma-valerolactone, which is supported on M-Beta zeolite (M=Sn, Ti, Zr or Hf) and is capable of converting unused saccharide-derived furfural into gamma-valerolactone, a high value-added compound, through a one-pot process.

In another aspect, the technique disclosed herein has an effect of providing a method for preparing the catalyst for producing gamma-valerolactone.

In still another aspect, the technique disclosed herein has an effect of providing a method for manufacturing gamma-valerolactone using the catalyst.

DETAILED DESCRIPTION OF THE PREFERRED EMBODIMENTS

Figure 1:
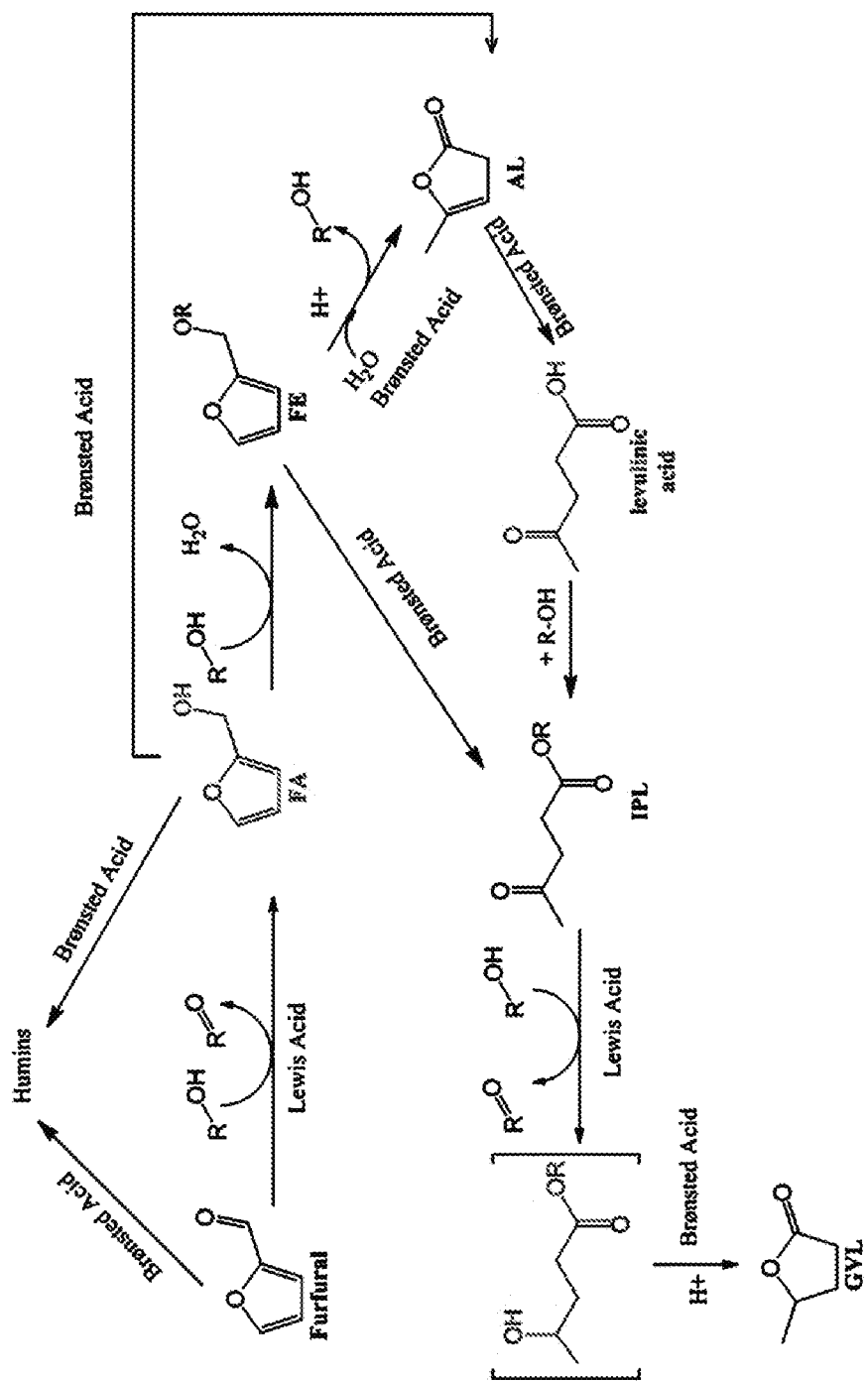
FIG. 1 illustrates the intermediates produced in the course of the conversion of furfural into gamma-valerolactone and the reaction path expected:
FA: Furfuryl Alcohol
FE: Furfuryl-propyl ether
AL: Angelica Lactone
LA: Levulinic Acid
IPL: Isopropyl Levulinate
GVL: γ-Valerolactone.

Hereinafter, the present invention will be described in detail.

In an aspect, the technique disclosed herein provides a catalyst for producing gamma-valerolactone, which contains Beta zeolite substituted with a metal; and a heteropolyacid supported on the zeolite.

In an exemplary embodiment, the metal may be one or more selected from Group 4 consisting of titanium (Ti), zirconium (Zr), and hafnium (Hf).

In an exemplary embodiment, the metal may be tin (Sn).

In an exemplary embodiment, the catalyst may contain M-Beta zeolite (where M is a metal and may be one or more selected from Group 4 consisting of titanium (Ti), zirconium (Zr), and hafnium (Hf) or tin (Sn)); and a heteropolyacid supported on the zeolite. The M-Beta zeolite means one in which the skeleton (Si/Al>150) of high-silica zeolite having a BEA structure is substituted with, for example, one or more metals of Sn, Ti, Zr or Hf. The Si/Al ratio of the high-silica zeolite can be controlled by the dealumination conditions of the Beta zeolite.

The catalyst has all the active sites for promoting the three steps of reactions (furfural hydrogenation reaction, furfuryl alcohol ring-opening reaction, and levulinic acid hydrogenation reaction) required for conversion of furfural into gamma-valerolactone and thus has an effect of producing gamma-valerolactone at a high yield through a one-pot process. More specifically, the metal contained in the M-Beta zeolite skeleton, for example, Sn, Ti, Zr or Hf metal plays a role of promoting the hydrogenation reaction of furfural and levulinic acid, and the heteropolyacid supported on the M-Beta zeolite acts as an active site for promoting the ring-opening reaction of furfuryl alcohol.

In an exemplary embodiment, the M-Beta zeolite may be prepared by a hydrothermal synthesis or post-synthesis method.

In an exemplary embodiment, the post-synthesis method may include synthesizing Al-Beta zeolite by a hydrothermal synthesis method; exposing the Al-Beta zeolite synthesized to an aqueous solution of nitric acid at a high concentration for dealumination; and mixing the dealuminated Si-Beta zeolite with a metal precursor and then performing a heat treatment to substitute the zeolite skeleton with a metal.

In an exemplary embodiment, the metal precursor may include one or more precursors selected from the group consisting of salts and oxysalts of metals and organometallic compounds.

In an exemplary embodiment, the heat treatment may be conducted at a temperature of 500° C. to 600° C. for 4 to 16 hours in an air atmosphere.

In an exemplary embodiment, the catalyst may be for producing gamma-valerolactone from furfural.

In an exemplary embodiment, the content of the metal may be 1 to 10 wt % based on the total weight of the catalyst. In another exemplary embodiment, the content of the metal may be 1 wt % or more, 2 wt % or more, 3 wt % or more, 4 wt % or more, 5 wt % or more, 6 wt % or more, 7 wt % or more and 10 wt % or less, 9 wt % or less, 8 wt % or less, 7 wt % or less, 6 wt % or less, 5 wt % or less, or 4 wt % or less based on the total weight of the catalyst.

The heteropolyacid is a condensed inorganic acid containing Tungsten (W), molybdenum (Mo), vanadium (V), niobium (Nb), and the like as a coordinating element and phosphorus (P), silicon (Si), germanium (Ge), arsenic (As), boron (B), cobalt (Co), and the like as a center element, and in an exemplary embodiment, the heteropolyacid may have a formula $H_nXM_{12}O_{40}$ where X may be a center element of phosphorus (P), silicon (Si), germanium (Ge) or arsenic (As), M may be a coordinating element including tungsten (W) or molybdenum (Mo), and n may be an integer more than 0. The heteropolyacid significantly increases the ring-opening reaction rate of furfuryl alcohol by its strong Brønsted acid character and thus has an effect of producing gamma-valerolactone at a high yield.

In an exemplary embodiment, the heteropolyacid may contain tungsten (W) or molybdenum (Mo).

In an exemplary embodiment, the heteropolyacid may be one or more selected from the group consisting of 12-tungstophosphoric acid ($H_3PW_{12}O_{40}$), 12-tungstosilicic acid ($H_4SiW_{12}O_{40}$), 12-molybdophosphoric acid ($H_3PMo_{12}O_{40}$), and 12-molybdosilicic acid ($H_4SiMo_{12}O_{40}$).

In an exemplary embodiment, the heteropolyacid may be supported in an amount of 1 to 10 parts by weight based on 100 parts by weight of the total weight of zeolite. In another exemplary embodiment, the heteropolyacid may be supported in an amount of 1 part by weight or more, 2 parts by weight or more, 3 parts by weight or more, 4 parts by weight or more, 5 parts by weight or more, 6 parts by weight or more, or 7 parts by weight or more and 10 parts by weight or less, 9 parts by weight or less, 8 parts by weight or less, 7 parts by weight or less, 6 parts by weight or less, 5 parts by weight or less, or 4 parts by weight or less based on 100 parts by weight of the total weight of zeolite.

In another aspect, the technique disclosed herein provides a method for preparing the catalyst for producing gamma-valerolactone described above, the method including: impregnating Beta zeolite substituted with a metal with a heteropolyacid solution; and calcining the impregnated catalyst.

In an exemplary embodiment, the solvent of the heteropolyacid solution may be an alcohol solvent having 1 to 6 carbon atoms.

In an exemplary embodiment, the impregnating method may be an incipient wetness impregnation in which a heteropolyacid solution in an amount corresponding to the pore volume of zeolite is gradually added to and supported on the zeolite.

In an exemplary embodiment, the method may include drying the impregnated catalyst in an air atmosphere prior to calcination.

In an exemplary embodiment, the calcination process may be conducted at a temperature of 100° C. to 400° C. in an air atmosphere. Accordingly, there is an effect of preventing the problem in which the organic substance contained in the impregnation solution is not easily removed due to the low calcination temperature. Also, it has an effect of preventing the problem in which the Keggin structure of the heteropolyacid is collapsed due to the high calcination temperature, thereby losing the Brønsted acid character and deteriorating the catalytic activity.

In another exemplary embodiment, the calcination process may be conducted at a temperature of 100° C. or higher, 120° C. or higher, 140° C. or higher, 160° C. or higher, 180° C. or higher, 200° C. or higher, 220° C. or higher, 240° C. or higher, 260° C. or higher, 280° C. or higher, 300° C. or higher, 320° C. or higher, 340° C. or higher, or 360° C. or higher and 400° C. or lower, 380° C. or lower, 360° C. or lower, 340° C. or lower, 320° C. or lower, 300° C. or lower, 280° C. or lower, 260° C. or lower, 240° C. or lower, 220° C. or lower, 200° C. or lower, 180° C. or lower, 160° C. or lower, or 140° C. or lower in an air atmosphere.

In still another aspect, the technique disclosed herein provides a method for manufacturing gamma-valerolactone, the method including: conducting a reaction for producing gamma-valerolactone using the catalyst for producing gamma-valerolactone described above.

In an exemplary embodiment, the reaction for producing gamma-valerolactone may be conducted by mixing furfural and an alcohol solvent with the catalyst.

In an exemplary embodiment, the alcohol solvent may be one or more selected from the group consisting of methanol, ethanol, isopropanol, butanol, pentanol, and hexanol.

In the method for manufacturing gamma-valerolactone according to the present specification, the alcohol functions not only as a reaction solvent but also as a hydrogen source for the hydrogenation reaction of furfural and levulinic acid. The Sn and Zr metals present in the zeolite skeleton of the catalyst for producing gamma-valerolactone play a role of promoting the hydrogen transfer reaction in which the hydrogen atoms of the alcohol molecules are directly transferred to the furfural and levulinic acid, which are reactants, and a reduction reaction proceeds.

In an exemplary embodiment, the reaction for producing gamma-valerolactone may be conducted at 120° C. to 180° C. Accordingly, there is an effect of preventing the problem in which the reaction conversion becomes too low due to the low reaction temperature. Also, it has an effect of preventing the problem in which the side reactions such as the polymerization reaction of furfural are promoted greatly due to the high reaction temperature, thereby lowering selectivity toward gamma-valerolactone.

In an exemplary embodiment, the reaction for producing gamma-valerolactone may be conducted for 6 to 48 hours.

Hereinafter, the present invention will be described in more detail with reference to Examples. It should be apparent to those skilled in the art that these embodiments are for illustrative purposes only and that the scope of the present invention is not construed as being limited by these examples.

EXAMPLE 1

Preparation of Catalyst for Producing Gamma-Valerolactone

M-Beta (M=Sn or Zr) zeolite was prepared by a post-synthesis method in which the zeolite skeleton is substituted with a metal through solid-state-ion-exchange with a metal precursor after the dealumination of Al-Beta zeolite.

Specifically, the dealumination process was performed by mixing commercially available Al-Beta zeolite (Si/Al=12.5, product of Zeolyst) and an aqueous solution of nitric acid (65 vol %) at a rate of 20 mL/g.cat and stirring the mixture at 80° C. for 24 hours. After stirring, the solid powder was separated from the liquid phase by vacuum filtration and then flush with distilled water multiple times to wash the solid powder. Thereafter, the solid powder was dried at 110° C. for 12 hours and then calcined at 500° C. in an air atmosphere to completely remove the residual nitrate ions ($NO_3^-$).

Dimethyltin dichloride (($CH_3$)$_2Cl_2Sn$) and bis(cyclopentadienyl)zirconium dichloride ($C_{10}H_{10}Cl_2Zr$) were used as metal precursors for solid-state-ion-exchange. For solid-state-ion-exchange, first 1 g of the dealuminated zeolite and the metal precursors were thoroughly mixed for 20 minutes using a mortar and pestle. Thereafter, the temperature of the solid mixture was raised to 550° C. at 5° C/min and calcined for 6 hours in an air atmosphere to substitute the zeolite skeleton with the metals. The catalyst finally prepared was named M-Beta zeolite (M=Sn or Zr) and various catalysts were prepared by changing the content ratio so that the metal content in the catalyst was 2.5 wt %, 5 wt %, 7.5 wt %, 10 wt %, and 15 wt %.

The heteropolyacid was supported on the M-Beta zeolites thus prepared by incipient wetness impregnation. As the heteropolyacid precursor, hydrates of 12-tungstophosphoric acid ($H_3PW_{12}O_{40}$, HPW), 12-tungstosilicic acid ($H_4SiW_{12}O_{40}$, HSiW), and 12-molybdophosphoric acid ($H_3PMo_{12}O_{40}$, HPMo) were purchased from Sigma Aldrich and used as received. First, the heteropolyacid hydrate was dissolved in ethanol in an amount corresponding to the incipient impregnation point volume of the M-Beta zeolite to prepare a mixed solution. The amount of the heteropolyacid hydrate was adjusted so that the content of heteropolyacid to be supported was 5 wt % and 10 wt % based on 1 g of M-Beta zeolite. Thereafter, the M-Beta zeolite was gradually impregnated with the heteropolyacid/ethanol mixed solution. After the impregnation was completed, the impregnated M-Beta zeolite was gradually dried at ambient condition for 24 hours so that the heteropolyacid was uniformly distributed into the pores of the M-Beta zeolite and then calcined in a drying oven at 100° C. for 24 hours, thereby preparing a catalyst.

Among the catalysts finally prepared, HPW/Zr-Beta, HSiW/Zr-Beta, and HPMo/Zr-Beta were used in the following experiments. HPW/Zr-Beta catalysts calcined at 350° C. and 450° C. in an air atmosphere were also prepared in order to investigate the effect of calcination temperature on the reaction activity for producing gamma-valerolactone.

Experimental Example 1

Experiment on Reaction for Producing Gamma-Valerolactone

The reaction for producing gamma-valerolactone was conducted in an 80 ml batch reactor. The catalyst (0.08 g) prepared in Example 1 was introduced into a reactor, and then 0.2 g of furfural mixed with 20 mL of isopropyl alcohol of a solvent was introduced into the reactor. Thereafter, the air contained in the reactor was thoroughly discharged from the reactor using nitrogen, then the nitrogen gas was filled in the reactor up to 10 bar, and the reaction temperature was raised to 120° C. to 140° C. while stirring the mixture using a magnetic stirrer. After the reaction temperature was achieved, the reaction was conducted for 6 hours, and the reaction products were analyzed by GC. FIG. 1 illustrates the reaction path expected based on the reaction products observed as a result of the catalytic reaction, and the quantitative analysis results of the reaction products are presented in Table 1.

From Table 1, it can be seen that the Zr-Beta catalysts supporting heteropolyacid (HPW/Zr-Beta and HSiW/Zr-Beta) produce gamma-valerolactone at high yields (20-23.0%) to be two times or more than that over the Zr-Beta catalyst (7-12%). In addition, the yield of gamma-valerolactone is greatly affected by the content of Zr and heteropolyacid in the catalyst, and the catalysts in which the contents of Zr and heteropolyacid are each 5% exhibited the highest gamma-valerolactone yield. Due to a short reaction time of 6 hours, various reaction intermediates were observed along with gamma-valerolactone, which is the final product of the reaction, and furfuryl-propyl ether (FE), angelica lactone (AL), and isopropyl levulinate (IPL) were the major reaction intermediates.

From FIG. 1, it is considered that furfural is first converted into furfuryl alcohol through a hydrogenation reaction on the Zr-Beta catalyst supporting heteropolyacid and then the furfuryl alcohol is rapidly converted into furfuryl-propyl ether (FE) through an etherification reaction with an alcohol solvent. Thereafter, the furfuryl-propyl ether may be directly converted into isopropyl levulinate (IPL) through a ring-opening reaction or forms angelica lactone (AL) and then the angelica lactone may be converted into isopropyl levulinate (IPL) via levulinic acid (LA) through a ring-opening reaction. Finally, isopropyl levulinate (IPL) is converted into gamma-valerolactone through a hydrogenation reaction using Zr metal as an active site.

In addition, according to Table 1, it can be seen that the yield of furfuryl-propyl ether (FE) is significantly high (20-37%) on the Sn-Beta or Zr-Beta catalyst which does not support heteropolyacid but the yield of furfuryl-propyl ether (FE) remarkably decreases (6-11%) on the Zr-Beta catalyst supporting heteropolyacid. Consequently, it can be seen that the heteropolyacid promotes the ring-opening reaction of furfuryl-propyl ether (FE) and thus increases the production yield of gamma-valerolactone.

TABLE 1

| | Catalyst | Reaction temperature (° C.) | Conversion ratio (%) | Yield (mol %) | | | | |
|---|---|---|---|---|---|---|---|---|
| | | | | GVL | FE | AL | LA | IPL |
| 1 | Sn-Beta 5% | 140 | 100 | 7.2 | 20.4 | 37.4 | 7.8 | 8.0 |
| 2 | Zr-Beta 2.5% | 140 | 100 | 10.2 | 28.7 | 24.8 | — | 6.9 |
| 3 | Zr-Beta 5% | 120 | 100 | 2.0 | 57.7 | 25.5 | — | 3.0 |
| 4 | Zr-Beta 5% | 140 | 100 | 12.4 | 22.2 | 26.6 | — | 2.6 |
| 4 | Zr-Beta 7.5% | 140 | 100 | 10.3 | 26.5 | 30.4 | — | 8.0 |
| 5 | Zr-Beta 15% | 140 | 100 | 6.9 | 37.0 | 27.7 | — | 5.0 |
| 6 | HPW 5%/ Zr-Beta 5% | 120 | 100 | 2.2 | 39.9 | 26.8 | — | 10.3 |
| 7 | HPW 5%/ Zr-Beta 5% | 140 | 100 | 23.0 | 6.3 | 28.2 | — | 3.1 |
| 8 | HPW 10%/ Zr-Beta 5% | 140 | 100 | 20.2 | 6.7 | 26.8 | — | 5.2 |
| 9 | HPW 10%/ Zr-Beta 10% | 140 | 100 | 13.2 | 11.5 | 32.8 | — | 10.8 |
| 10 | HSiW 5%/ Zr-Beta 5% | 140 | 100 | 20.3 | 9.8 | 28.6 | — | 2.6 |

Experimental Example 2

Effect of Reaction Time on Gamma-Valerolactone Production

The reaction for producing gamma-valerolactone was conducted by the same method as in Experimental Example 1 except that Zr-Beta 5%, HPW 5%/Zr-Beta 5% or HSiW 5%/Zr-Beta 5% were used as a catalyst. The reaction products were analyzed by GC while fixing the reaction temperature at 140° C. but changing the reaction time to 1.5, 6, 12 to 48 hours. The quantitative analysis results of the reaction products depending on the reaction time are illustrated in FIG. 2.

Figure 2:
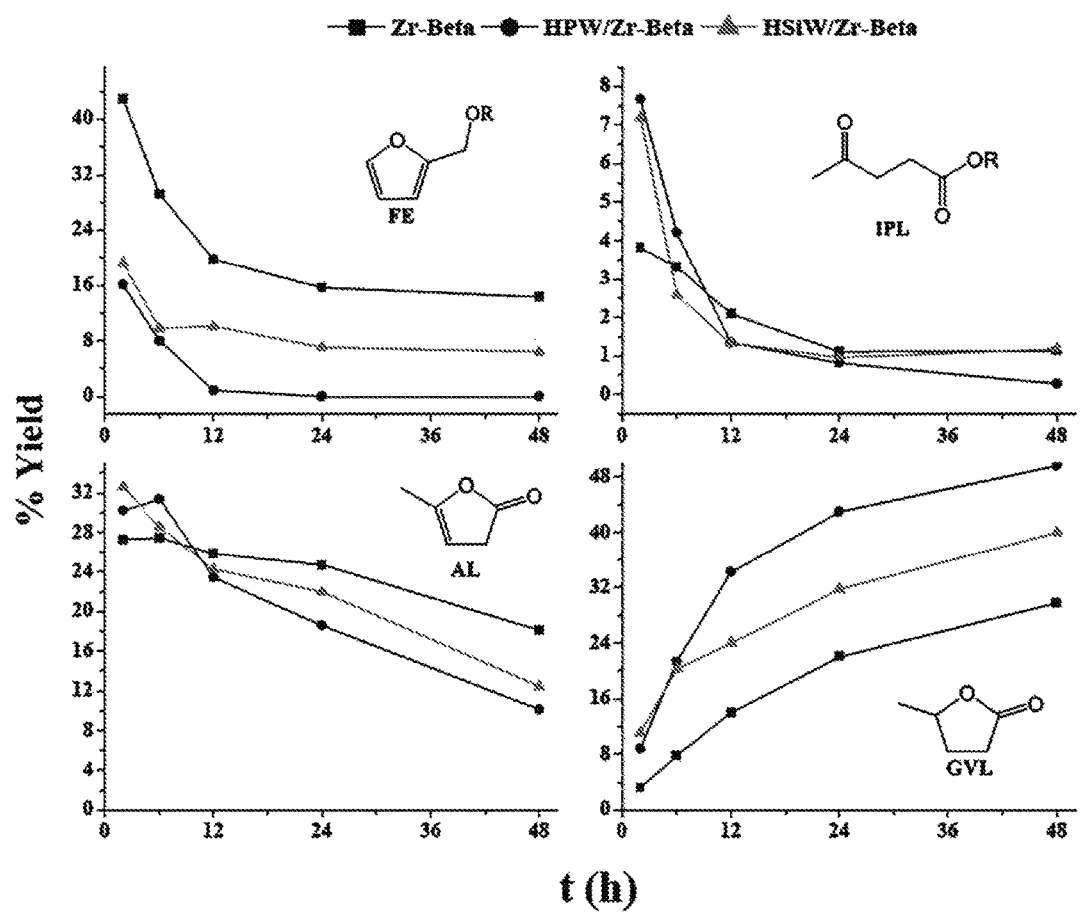
FIG. 2 illustrates the quantitative analysis results of reaction products depending on the reaction time in the reaction for producing gamma-valerolactone according to an experimental example of the present specification.

From FIG. 2, it can be seen that the yield of reaction intermediates such as furfuryl-propyl ether (FE) and isopropyl levulinate (IPL) decreases but the yield of gamma-valerolactone increases as the reaction time increases. It can be seen that the yield of gamma-valerolactone produced on the Zr-Beta (HPW/Zr-Beta) catalyst supporting heteropolyacid is about 50% after 48 hours of reaction and this is significantly higher than the yield (28%) by the Zr-Beta catalyst which does not support heteropolyacid.

Experimental Example 3

Effect of Kind of Heteropolyacid in Catalyst for Producing Gamma-Valerolactone

The reaction for producing gamma-valerolactone was conducted by the same method as in Experimental Example 1 except that HPW 5%/Zr-Beta 5%, HSiW 5%/Zr-Beta 5% or HPMo 5%/Zr-Beta 5% were used as a catalyst and the amount of catalyst used was increased to 0.2 g. After the reaction was conducted at 160° C. for 24 hours, the reaction products were analyzed by GC. The quantitative analysis results of the reaction products are presented in Table 2.

From Table 2, it can be seen that the production yield of gamma-valerolactone is affected by the kind of heteropolyacid (HPW, HSiW and HPMo) to some extent but the difference is not significant. It is considered that this is because the heteropolyacids used all have a Keggin structure and have strong Brønsted acid character.

TABLE 2

| | Catalyst | Reaction temperature (° C.) | Reaction time (h) | Conversion ratio (%) | Yield (%) | | | |
|---|---|---|---|---|---|---|---|---|
| | | | | | GVL | FE | AL | IPL |
| 1 | HPW 5%/Zr-Beta 5% | 160 | 24 | 100 | 67.3 | — | 1.7 | 3.2 |
| 2 | HSiW 5%/Zr-Beta 5% | 160 | 24 | 100 | 65.2 | 2.3 | 1.1 | 3.3 |
| 3 | HPMo 5%/Zr-Beta 5% | 160 | 24 | 100 | 63.4 | — | 1.3 | 3.0 |

Experimental Example 4

Effect of Calcination Temperature of Catalyst

The reaction for producing gamma-valerolactone was conducted by the same method as in Experimental Example 3 except that HPW 5%/Zr-Beta 5% and HSiW 5%/Zr-Beta 5% catalysts calcined at different temperatures (100° C., 350° C. and 450° C.) were used as a catalyst. The quantitative analysis results of the reaction products analyzed after the reaction was conducted at 160° C. for 24 hours are presented in Table 3.

From Table 3, it can be seen that the activity of the catalyst for producing gamma-valerolactone greatly changes depending on the calcination temperature of the catalyst. The HPW 5%/Zr-Beta 5% and HSiW 5%/Zr-Beta 5% catalysts both exhibited the highest production yield (up to 75%) of gamma-valerolactone when calcined at 350° C. It is considered that the reason for a decrease in the activity of the catalysts calcined at 450° C. is because the Keggin structure of the heteropolyacid begins to collapse, and the acid strength is decreased when the heat treatment is conducted at a temperature of 400° C. or higher.

TABLE 3

| | Catalyst | Calcination temperature (° C.) | Conversion ratio (%) | Yield (%) | | | |
|---|---|---|---|---|---|---|---|
| | | | | GVL | FE | AL | IPL |
| 1 | HPW 5%/Zr-Beta 5% | 100 | 100 | 67.3 | — | 1.7 | 3.2 |
| 2 | HPW 5%/Zr-Beta 5% | 350 | 100 | 71.2 | — | — | 2.9 |
| 3 | HPW 5%/Zr-Beta 5% | 450 | 100 | 61.9 | — | 0.9 | — |
| 4 | HSiW 5%/Zr-Beta 5% | 350 | 100 | 75.9 | — | — | 3.5 |
| 5 | HSiW 5%/Zr-Beta 5% | 450 | 100 | 68.8 | — | 1.3 | — |

Specific portions of the present invention have been described in detail, but it will be apparent to those skilled in the art that these specific descriptions are merely preferred embodiments and that the scope of the present invention is not limited thereby. Accordingly, the actual scope of the present invention will be defined by the appended claims and their equivalents.

What is claimed is:

1. A catalyst for producing gamma-valerolactone, comprising Beta zeolite substituted with a metal; and a heteropolyacid supported on the zeolite.

2. The catalyst for producing gamma-valerolactone according to claim 1, wherein the metal is one or more selected from Group 4 consisting of titanium (Ti), zirconium (Zr), and hafnium (Hf).

3. The catalyst for producing gamma-valerolactone according to claim 1, wherein the metal is tin (Sn).

4. The catalyst for producing gamma-valerolactone according to claim 1, wherein the zeolite substituted with a metal is prepared by a method including removing aluminum from Al-Beta zeolite and mixing the dealuminated Si-Beta zeolite with a metal precursor and then performing a heat treatment to substitute the zeolite skeleton with a metal.

5. The catalyst for producing gamma-valerolactone according to claim 1, wherein the catalyst is for producing gamma-valerolactone from furfural.

6. The catalyst for producing gamma-valerolactone according to claim 1, wherein a content of the metal is 1 to 10 wt % based on a total weight of the catalyst.

7. The catalyst for producing gamma-valerolactone according to claim 1, wherein the heteropolyacid has a formula $H_nXM_{12}O_{40}$ where X is a center element of phosphorus (P), silicon (Si), germanium (Ge) or arsenic (As), M is a coordinating element including tungsten (W) or molybdenum (Mo), and n is an integer more than 0.

8. The catalyst for producing gamma-valerolactone according to claim 7, wherein the heteropolyacid is one or more selected from the group consisting of 12-tungstophosphoric acid ($H_3PW_{12}O_{40}$), 12-tungstosilicic acid ($H_4SiW_{12}O_{40}$), 12-molybdophosphoric acid ($H_3PMo_{12}O_{40}$), and 12-molybdosilicic acid ($H_4SiMo_{12}O_{40}$).

9. The catalyst for producing gamma-valerolactone according to claim 1, wherein the heteropolyacid is supported in an amount of 1 to 10 parts by weight based on 100 parts by weight of a total weight of zeolite.

10. A method for preparing the catalyst for producing gamma-valerolactone according to claim 1, the method comprising:

impregnating Beta zeolite substituted with a metal with a heteropolyacid solution; and calcining the impregnated catalyst.

11. The method for preparing the catalyst for producing gamma-valerolactone according to claim 10, wherein a solvent of the heteropolyacid solution is an alcohol solvent having 1 to 6 carbon atoms.

12. The method for preparing the catalyst for producing gamma-valerolactone according to claim 10, wherein the impregnating method is an incipient wetness impregnation in which a heteropolyacid solution in an amount corresponding to a pore volume of zeolite is gradually added to and supported on the zeolite.

13. The method for preparing the catalyst for producing gamma-valerolactone according to claim 10, wherein a calcination temperature is 100° C. to 400° C.

14. A method for manufacturing gamma-valerolactone, the method comprising: conducting a reaction for producing gamma-valerolactone using the catalyst for producing gamma-valerolactone according to claim 1.

15. The method for manufacturing gamma-valerolactone according to claim 14, wherein the reaction for producing gamma-valerolactone is conducted by mixing furfural and an alcohol solvent with the catalyst.

16. The method for manufacturing gamma-valerolactone according to claim 14, wherein the reaction for producing gamma-valerolactone is conducted at 120° C. to 180° C.

17. The method for manufacturing gamma-valerolactone according to claim 14, wherein the reaction for producing gamma-valerolactone is conducted for 6 to 48 hours.

\* \* \* \* \*